United States Patent
Krieger et al.

(10) Patent No.: US 6,437,215 B1
(45) Date of Patent: Aug. 20, 2002

(54) SR-BI AND APOE KNOCKOUT ANIMALS AND USE THEREOF AS MODELS FOR ATHEROSCLEROSIS AND HEART ATTACK

(75) Inventors: Monty Krieger, Needham, MA (US); Jay M. Edelberg, New York, NY (US); Bernardo Trigatti, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/606,324

(22) Filed: Jun. 28, 2000

Related U.S. Application Data

(60) Provisional application No. 60/141,361, filed on Jun. 28, 1999, and provisional application No. 60/164,679, filed on Nov. 10, 1999.

(51) Int. Cl.[7] .................. A01K 67/027; G01N 33/00
(52) U.S. Cl. ................. 800/18; 800/3; 800/9
(58) Field of Search .............. 800/3, 9, 13, 14, 800/18

(56) References Cited

PUBLICATIONS

Prelle et al (1999) Cells Tissues Organs 165, 220–236.*
Moreadith et al (1997) J. Mol. Med. 75, 208–216.*
Rigotti et al (1997) Proced. Natl. Acad. Sci. 94, 12610–12615.*
Zhang et al (1992) Science259 468–471.*

* cited by examiner

*Primary Examiner*—Deborah Crouch
(74) *Attorney, Agent, or Firm*—Holland & Knight LLP

(57) ABSTRACT

Transgenic animals that do not express functional SR-BI and ApoE develop severe atherosclerosis, by age four weeks in transgenic mice. Moreover, these animals exhibit progressive heart block by age four weeks, and die by age nine weeks. Pathology shows extensive fibrosis of the heart and occlusion of coronary arteries. The occlusion appears to be due to clotting, since fat deposition is in the walls. These animals are good models for the following diseases, and for screening of drugs useful in the treatment and/or prevention of these disorders: cardiac fibrosis, myocardial infarction, defects in electrical conductance, atherosclerosis, unstable plaque, and stroke. In contrast to other known models for atherosclerosis, these animals do not have to be fed extreme diets for long periods before developing atherosclerosis. No other known model for heart attacks and stroke is known.

9 Claims, No Drawings

SR-BI AND APOE KNOCKOUT ANIMALS AND USE THEREOF AS MODELS FOR ATHEROSCLEROSIS AND HEART ATTACK

This application claims the benefit of U.S. Provisional Application No. 60/141,361, filed Jun. 28, 1999 and 60/164,679, filed Nov. 10, 1999.

STATEMENT REGARDING FEDERALLY SPONSORED RESEARCH

The U.S. government has certain rights to this invention by virtue of Grants HL41484, HI-52212, and HL20948 from the National Institutes of Health-National Heart, Lung and Blood Institute to Monty Kreiger.

BACKGROUND OF THE INVENTION

The present invention is generally in the area of transgenic animal models of atherosclerosis and methods for screening for inhibitors acting via interaction with the SR-BI scavenger receptor.

The intercellular transport of lipids through the circulatory system requires the packaging of these hydrophobic molecules into water-soluble carriers, called lipoproteins, and the regulated targeting of these lipoproteins to appropriate tissues by receptor-mediated pathways. The most well characterized lipoprotein receptor is the LDL receptor, which binds to apolipoproteins B-100 (apoB-100) and E (apoE), which are constituents of low density lipoprotein (LQL), the principal cholesteryl-ester transporter in human plasma, very low- density lipoprotein (VLDL), a triglyceride-rich carrier synthesized by the liver, intermediate-density lipoprotein (IDL), and catabolized chylomicrons (dietary triglyceride-rich carriers).

All members of the LDL receptor gene family consist of the same basic structural motifs. Ligand-binding (complement-type) cysteine-rich repeats of approximately 40 amino acids are arranged in clusters (ligand-binding domains) that contain between two and eleven repeats. Ligand-binding domains are always followed by EGF-precursor homologous domains. In these domains, two EGF-like repeats are separated from a third EGF-repeat by a spacer region containing ihe YWTD motif. In LRP and gp330, EGF-precursor homologous domains are either followed by another ligand-binding domain or by a spacer region. The EGF-precursor homology domain, which precedes the plasma membrane, is separated from the single membrane-spanning segment either by an O-linked sugar domain (in the LDL receptor and VLDL receptor) or by one (in C. elegans and gp330) or six EGF-repeats (in LRP). The cytoplasmic tails contain between one and three "NPXY" internalization signals required for clustering of the receptors in coated pits. In a later compartment of the secretory pathway, LRP is cleaved within the eighth EGF-precursor homology domain. The two subunits LRP-515 and LRP-85 (indicated by the brackets) remain tightly and non-covalently associated. Only partial amino acid sequence of the vitellogenin receptor and of gp330 are available.

LDL receptors and most other mammalian cell-surface receptors that mediate binding and, in some cases, the endocytosis, adhesion, or signaling exhibit two common ligand-binding characteristics: high affinity and narrow specificity. However, two additional lipoprotein receptors have been identified which are characterized by high affinity and broad specificity: the macrophage scavenger receptors class A type I and type II.

Scavenger receptors mediate the endocytosis of chemically modified lipoproteins, such as acetylated LDL (AcLDL) and oxidized LDL (OxLDL), and have been implicated in the pathogenesis of atherosclerosis (Krieger and Herz, 1994 Annu. Rev. Biochem. 63, 601-637; Brown and Goldstein, 1983 Annu. Rev. Biochem. 52, 223–261; Steinberg et al., 1989 N. Engl. J. Med. 320, 915–924). Macrophage scavenger receptors exhibit complex binding properties, including inhibition by a wide variety of polyanions, such as maleylated BSA (M-BSA) and certain polynucleotides and polysaccharides, as well as unusual ligand-cross competition (Freeman et al., 1991 Proc. Natl. Acad Sci. U.S.A. 88, 4931–4935, Krieger and Herz, 1994). Several investigators have suggested that there may be at least three different classes of such receptors expressed on mammalian macrophages, including receptors which recognize either AcLDL or OxLDL, or both of these ligands (Sparrow et al., 1989. J Biol. Chem 264, 2599–2604; Arai et al., 1989 Biochem. Biophys. Res. Commun. 159, 1375–1382; Nagelkerke et al., 1983 J Biol. Chem. 258, 12221–12227).

The first macrophage scavenger receptors to be purified and cloned were the mammalian class A type I and II receptors. These are trimeric integral membrane glycoproteins whose extracellular domains have been predicted to include a-helical coiled-coil, collagenous and globular structures (Kodama et al., 1990 Nature 343, 531–535; Rohrer et al., 1990 Nature 343, 570–572; Krieger and Herz, 1994). The collagenous domain, shared by the class A type I and type II receptors, apparently mediates the binding of polyanionic ligands (Acton et al., 1993 J Biol. Chem. 268, 3530–3537; Doi et al., 1993 J Biol. Chem. 268, 2126–2133). The class A type I and type II molecules, which are the products of alternative splicing of a single gene, are hereafter designated class A-scavenger receptors (SR-Al and SR-All). The class A receptors, which bind both AcLDL and OxLDL (Freeman et al., 1991), have been proposed to be involved in host defense and cell adhesion, as well as atherogenesis (Freeman et al., 1991; Krieger, 1992 Trends Biochem. Sci. 17, 141–146; Fraser et al., 1993 Nature 364, 343–346; Krieger and Herz, 1994).

Based on models of the predicted quaternary structures of the class A type I and type II macrophage scavenger receptors, both contain six domains, of which the first five are identical: the N-terminal cytoplasmic region, the transmembrane region, spacer, a-helical coil, and collagen-like domains. The C-terminal sixth domain of the type I receptor is composed of an eight-residue spacer followed by a 102-amino acid cysteine-rich domain (SRCR), while the sixth domain of the type II receptor is only a short oligopeptide.

Using a murine macrophage cDNA library and a COS cell expression cloning technique, Endemann, Stanton and colleagues, (Endemann, et al. 1993 J. Biol. Chem. 268, 11811–11816; Stanton, et al. J. Biol. Chem. 267, 22446–22451), reported the cloning of cDNAs encoding two additional proteins that can bind OxLDL. The binding of OxLDL to these proteins was not inhibited by AcLDL. These proteins are FcgRII-B2 (an Fc receptor) (Stanton et al., 1992) and CD36 (Endemann et al., 1993). The significance of the binding of OxLDL to FcgRII-B2 in transfected COS cells is unclear because FcgRII-B2 in macrophages apparently does not contribute significantly to OxLDL binding (Stanton et al., 1992). However, CD36 may play a quantitatively significant role in OxLDL binding by macrophages (Endemann et al., 1993). In addition to binding oxidized LDL, CD36 binds thrombospondin (Asch et al., 1987 J Clin. Invest. 79, 1054–1061), collagen (Tandon et al., 1989 J Biol. Chem. 264, 7576–7583), long-chain fatty acids (Abumrad et al., 1993 J Biol. Chem. 268, 17665–17668) and Plasmodium falciparum infected erythrocytes (Oquendo et al., 1989 Cell 58, 95–101). CD36 is expressed in a variety of tissues, including adipose, and in macrophages, epithelial cells, monocytes, endothelial cells, platelets, and a wide variety of cultured lines (Abumrad et al., 1993; and see Greenwalt et al., 1992 Blood 80, 1105–1115 for review). Although the physiologic functions of CD36 are not known, it may serve as an adhesion molecule due to its collagen-binding properties. It is also been proposed to be a long-chain fatty acid transporter (Abumrad et al., 1993) and a signal transduction molecule (Ockenhouse et al., 1989 J Clin. Invest. 84,468–475; Huang et al., 1991 Proc. Natl. Acad. Sci. USA 88, 7844–7848), and may serve as a receptor on macrophages for senescent neutrophils (Savill et al., 1991 Chest 99, 7 (suppl)).

Modified lipoprotein scavenger receptor activity has also been observed in endothelial cells (Arai et al., 1989; Nagelkerke et al., 1983; Brown and Goldstein, 1983; Goldstein et al., 1979 Proc. Natl. Acad. Sci. U.S.A. 76, 333–337). At least some of the endothelial cell activity apparently is not mediated by the class A scavenger receptors (Bickel et al., 1992 J Clin. Invest. 90, 1450–1457; Arai et al., 1989; Nagelkerke et al., 1983; Via et al., 1992 The Faseb J. 6, A371), which are often expressed by macrophages (Naito et al., 1991 Am. J. Pathol. 139, 1411–1423; Krieger and Herz, 1994). In vivo and in vitro studies suggest that there may be scavenger receptor genes expressed in endothelial cells and macrophages which differ from both the class A scavenger receptors and CD36 (Haberland et al., 1986 J. Clin. Inves. 77, 681–689; Via et al., 1992; Sparrow et al., 1989; Horiuchi et al., 1985 J Biol. Chem. 259, 53–56; Arai et al., 1989; and see below). Via, Dressel and colleagues (Ottnad et al., 1992 Biochem J. 281, 745–751) and Schnitzer et al. 1992 J. Biol. Chem. 267, 24544–24553) have detected scavenger receptor-like binding by relatively small membrane associated proteins of 15–86 kD. In addition, the LDL receptor related protein (LRP) has been shown to bind lipoprotein remnant particles and a wide variety of other macromolecules. Both the MRNA encoding LRP and the LRP protein are found in many tissues and cell types (Herz, et al., 1988 EMBO J. 7:4119–4127; Moestrup, et al., 1992 Cell Tissue Res. 269:375–382), primarily the liver, the brain and the placenta. The predicted protein sequence of the LRP consists of a series of distinctive domains or structural motifs, which are also found in the LDL receptor.

As described by Kreiger, et al., in PCT/US95/07721 "Class BI and CI Scavenger Receptors" Massachusetts Institute of Technology ("Krieger, et al."), two distinct scavenger receptor type proteins having high affinity for modified lipoproteins and other ligands have been isolated, characterized and cloned. Hamster and murine homologs of SR-BI, an AcLDL and LDL binding scavenger receptor, which is distinct from the class A type I and type II macrophage scavenger receptors, has been isolated and characterized. In addition, DNA encoding the receptor cloned from a variant of Chinese Hamster Ovary Cells, designated Var-261, has been isolated and cloned. dSR-CI, a non-mammalian AcLDL binding scavenger receptor having high ligand affinity and broad specificity, was isolated from Drosophila melanogaster.

It was reported by Kreiger, et al. that the SR-BI receptor is expressed principally in steroidogenic tissues and liver and appears to mediate HDL-transfer and uptake of cholesterol. Competitive binding studies show that SR-BI binds LDL, modified LDL, negatively charged phospholipid, and HDL. Direct binding studies show that SR-BI expressed in mammalian cells (for example, a varient of CHO cells) binds HDL, without cellular degradation of the HDL-apoprotein, and lipid is accumulated within cells expressing the receptor. These studies indicate that SR-BI might play a major role in transfer of cholesterol from peripheral tissues, via HDL, into the liver and steroidogenic tissues, and that increased or decreased expression in the liver or other tissues may be useful in regulating uptake of cholesterol by cells expressing SR-BI, thereby decreasing levels in foam cells and deposition at sites involved in atherogenesis.

Atherosclerosis is the leading cause of death in western industrialized countries. The risk of developing atherosclerosis is directly related to plasma levels of LDL cholesterol and inversely related to HDL cholesterol levels. Over 20 years ago, the pivotal role of the LDL receptor in LDL metabolism was elucidated by Goldstein, et al., in the Metabolic and Molecular Bases of Inherited Disease, Scriver, et al. (McGraw-Hill, NY 1995), pp. 1981–2030. In contrast, the cellular mechanisms responsible for HDL metabolism are still not well defined. It is generally accepted that HDL is involved in the transport of cholesterol from extrahepatic tissues to the liver, a process known as reverse cholesterol transport, as described by Pieters, et al., Biochim. Biophys. Acta 1225, 125 (1994), and mediates the transport of cholesteryl ester to steroidogenic tissues for hormone synthesis, as described by Andersen and Dietschy, J Biol. Chem. 256, 7362 (1981). The mechanism by which HDL cholesterol is delivered to target cells differs from that of LDL. The receptor-mediated metabolism of LDL has been thoroughly described and involves cellular uptake and degradation of the entire particle. In contrast, the receptor-mediated HDL metabolism has not been understood as well. Unlike LDL, the protein components of HDL are not degraded in the process of transporting cholesterol to cells. Despite numerous attempts by many investigators, the cell-surface protein(s) that participate in the delivery of cholesterol from HDL to cells had not been identified before the discovery that SR-BI was an HDL receptor.

It is an object of the present invention to provide methods and reagents for designing drugs that can stimulate or inhibit the binding to and lipid movements mediated by SR-BI and redirect uptake and metabolism of lipids and cholesterol by cells.

SUMMARY OF THE INVENTION

Transgenic animals that do not express functional SR-BI and ApoE develop severe atherosclerosis, by age four weeks in transgenic mice. Moreover, these animals exhibit progressive heart block by age four weeks, and die by age nine weeks. Pathology shows extensive fibrosis of the heart and occlusion of coronary arteries. The occlusion appears to be due to clotting, since fat deposition is in the walls. Equivalent animals can be produced using single knockout animals with an inhibitor, for example, an inhibitor of SR-BI administered to an ApoE knockout, or verse versa. These animals are good models for the following diseases, and for screening of drugs useful in the treatment and/or prevention of these disorders: cardiac fibrosis, myocardial infarction, defects in electrical conductance, atherosclerosis, unstable plaque, and stroke. In contrast to other known models for atherosclerosis, these animals do not have to be fed extreme diets for long periods before developing atherosclerosis. No other known model for heart attacks and stroke is known.

DETAILED DESCRIPTION OF THE INVENTION

The role of SR-BI has now been confirmed as the principle mediator of cholesteryl ester transport from peripheral tissues to the liver and other steroidogenic tissues, including the adrenal gland, testes and ovaries. The studies described herein demonstrate that animals which are deficient in both SR-BI and ApoE are not only excellent models for atherosclerosis but also myocardial infarction and stroke, since the animals develope progressive heart block and coronary artery occlusions characterized by clots resembling those in heart attack patients.

These animals can be used to screen for drugs that are effective as therapeutics or diagnostics of heart disease.

Pharmaceutical Compositions

Compounds are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. No. 4,906,474, 4,925,673, and 3,625,214.

The pharmaceutical compositions are administered in an effective amount effective to modify or treat the disorder. These are readily determined by measuring blood, urine and/or tissue samples using clinically available tests. The exact dosages can be determined based on the use of animal models which are accepted as predictive of the effects of drugs on steroid levels, for example, of contraceptives or cortisone.

Generation of Transgenic Animals for Screening

With the knowledge of the cDNA encoding SR-BI and regulatory sequences regulating expression thereof, it is possible to generate transgenic animals, especially rodents, for testing the compounds which can alter SR-BI expression, translation or function in a desired manner. This procedure for transient overexpression in animals following infection with adenoviral vectors is described below in the examples.

There are basically two types of animals which are useful: those not expressing functional SR-BI, which are useful for testing of drugs which may work better in combination with an inhibitor of SR-BI to control levels of lipid, cholesterol, lipoprotein or components thereof, and those which overexpress SR-BI, either in those tissues which already express the protein or in those tissues where only low levels are naturally expressed.

The animals in the first group are preferably made using techniques that result in "knocking out" of the gene for SR-BI, although in the preferred case this will be incomplete, either only in certain tissues, or only to a reduced amount. These animals are preferably made using a construct that includes complementary nucleotide sequence to the SR-BI gene, but does not encode functional SR-BI, and is most preferably used with embryonic stem cells to create chimeras. Animals which are heterozygous for the defective gene can also be obtained by breeding a homozygote normal with an animal which is defective in production of SR-BI. These animals can then be crossed with other transgenic or knockout animals, as described in the following examples. Equivalent animals can be produced using single knockout animals with an inhibitor, for example, an inhibitor of SR-BI administered to an ApoE knockout, or verse versa.

The animals in the second group are preferably made using a construct that includes a tissue specific promoter, of which many are available and described in the literature, or an unregulated promoter or one which is modified to increase expression as compared with the native promoter. The regulatory sequences for the SR-BI gene can be obtained using standard techniques based on screening of an appropriate library with the cDNA encoding SR-BI. These animals are most preferably made using standard microinjection techniques.

These manipulations are performed by insertion of cDNA or genomic DNA into the embryo using microinjection or other techniques known to those skilled in the art such as electroporation, as described below. The DNA is selected on the basis of the purpose for which it is intended: to inactivate the gene encoding an SR-BI or to overexpress or express in a different tissue the gene encoding SR-BI. The SR-BI encoding gene can be modified by homologous recombination with a DNA for a defective SR-BI, such as one containing within the coding sequence an antibiotic marker, which can then be used for selection purposes.

Animal Sources

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats.

Microinjection Procedures

The procedures for manipulation of the embryo and for microinjection of DNA are described in detail in Hogan et al. Manipulating the mouse embryo, Cold Spring Harbor Laboratory, Cold Spring Harbor, N.Y. (1986), the teachings of which are incorporated herein. These techniques are readily applicable to embryos of other animal species, and, although the success rate is lower, it is considered to be a routine practice to those skilled in this art.

Transgenic Animals

Female animals are induced to superovulate using methodology adapted from the standard techniques used with mice, that is, with an injection of pregnant mare serum gonadotrophin (PMSG; Sigma) followed 48 hours later by an injection of human chorionic gonadotrophin (hCG; Sigma). Females are placed with males immediately after hCG injection. Approximately one day after hCG, the mated females are sacrificed and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult females are mated with vasectomized males to induce a false pregnancy, at the same time as donor females. At the time of embryo transfer, the recipient females are anesthetized and the oviducts are exposed by an incision through the body wall directly over the oviduct. The ovarian bursa is opened and the embryos to be transferred are inserted into the infundibulum. After the transfer, the incision is closed by suturing.

Embryonic Stem (ES) Cell Methods
Introduction of cDNA into ES cells:

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E.J. Robertson, (IRL Press 1987), the teachings of which are incorporated herein. Selection of the desired clone of transgene-containing ES cells is accomplished through one of several means. In cases involving sequence specific gene integration, a nucleic acid sequence for recombination with the SR-BI gene or sequences for controlling expression thereof is co-precipitated with a gene encoding a marker such as neomycin resistance. Transfection is carried out by one of several methods described in detail in Lovell-Badge, in *Teratocarcinomas and embryonic stem cells, a practical approach*, ed. E.J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. In these procedures, a number of ES cells, for example, $0.5 \times 10^6$, are plated into tissue culture dishes and transfected with a mixture of the linearized nucleic acid sequence and 1 mg of pSV2neo DNA (Southern and Berg, *J Mol. Appl. Gen.* 1:327–341 (1982)) precipitated in the presence of 50 mg lipofectin in a final volume of 100 μl. The cells are fed with selection medium containing 10% fetal bovine serum in DMEM supplemented with an antibiotic such as G418 (between 200 and 500 pg/ml). Colonies of cells resistant to G418 are isolated using cloning rings and expanded. DNA is extracted from drug resistant clones and Southern blotting experiments using the nucleic acid sequence as a probe are used to identify those clones carrying the desired nucleic acid sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150–153 (1989)). DNA introduction by electroporation is less efficient and requires a selection step. Methods for positive selection of the recombination event (i.e., neo resistance) and dual positive-negative selection (i.e., neo resistance and ganciclovir resistance) and the subsequent identification of the desired clones by PCR have been described by Joyner et al., *Nature* 338, 153–156 (1989) and Capecchi, (1989), the teachings of which are incorporated herein.

Embryo Recovery and ES Cell Injection

Naturally cycling or superovulated females mated with males are used to harvest embryos for the injection of ES cells. Embryos of the appropriate age are recovered after successful mating. Embryos are flushed from the uterine horns of mated females and placed in Dulbecco's modified essential medium plus 10% calf serum for injection with ES cells. Approximately 10–20 ES cells are injected into blastocysts using a glass microneedle with an internal diameter of approximately 20 μm.

Transfer of Embryos to Pseudopregnant Females

Randomly cycling adult females are paired with vasectomized males. Recipient females are mated such that they will be at 2.5 to 3.5 days post-mating (for mice, or later for larger animals) when required for implantation with blastocysts containing ES cells. At the time of embryo transfer, the recipient females are anesthetized. The ovaries are exposed by making an incision in the body wall directly over the oviduct and the ovary and uterus are externalized. A hole is made in the uterine horn with a needle through which the blastocysts are transferred. After the transfer, the ovary and uterus are pushed back into the body and the incision is closed by suturing. This procedure is repeated on the opposite side if additional transfers are to be made.

Identification of Transgenic Animals

Samples (1–2 cm of mouse tails) are removed from young animals. For larger animals, blood or other tissue can be used. To test for chimeras in the homologous recombination experiments, i.e., to look for contribution of the targeted ES cells to the animals, coat color has been used in mice, although blood could be examined in larger animals. DNA is prepared and analyzed by both Southern blot and PCR to detect transgenic founder ($F_0$) animals and their progeny ($F_1$ and $F_2$).

Once the transgenic animals are identified, lines are established by conventional breeding and used as the donors for tissue removal and implantation using standard techniques for implantation into humans.

The present invention will be further understood by reference to the following non-limiting examples.

Example 1

Production and Characterization of Transgenic Animals Which do not Express SR-BI To determine directly if SR-BI normally plays an important role in HDL metabolism in vivo and to establish an experimental system to examine the role of SR-BI in pathologic states, mice containing a targeted null mutation in the gene encoding SR-BI were generated.

Materials and Methods
Generation of SR-BI mutant mice.

SR-BI genomic DNA was isolated from a mouse strain 129 DNA library (Genome Systems, St. Louis, Mo.), and screened by PCR amplification using primer pairs corresponding to the 5' and 3' ends of the mSR-BI cDNA. From one clone a 12 kb Xba I fragment containing the first coding exon was identified. A replacement-type targeting vector, containing 0.75 kb and 9 kb short and long homology regions and the pol2sneobpA and herpes simplex virus thymidine kinase (TK) cassettes, was constructed using standard methods. The vector was linearized and 100 μg were transfected by electroporation (240 V, 500 μF) into $112\times10^6$ murine D3 embryonic stem cells, which were then plated onto irradiated mouse embryonic fibroblast feeder layers. After G418/gancyclovir positive/negative selection for 7–8 days, 492 of the 5800 surviving colonies were picked and screened by PCR analysis using primers specific for the targeted allele (primer 1 5'-TGAAGGTGGTCTTCAAGAGCAGTCCT-3' (SEQ ID NO:5); and primer 3 5'-GATTGGGAAGACAATAGCAGGCATGC-3' (SEQ ID NO:6); all oligonucleotide primers were synthesized by Research Genetics). The presence of the targeted allele (amplification of a 1.4 kb band) was confirmed by Southern blot analysis of Xba I digested genomic DNA using probes that yielded either the predicted 12 kb fragment characteristic of the wild-type allele or the predicted 2.5 kb and 9 kb fragments from the targeted mutant allele. Bam HI digested genomic DNA was also probed with a 0.9 kb fragment derived by Pst I digestion of the neomycin resistance gene cassette to confirm the presence of a single neo gene in the mutant cells. Embryonic stem cell clones containing a disrupted SR-BI allele were injected into C57BL/6 blastocysts, which were implanted into recipient females. The resulting chimeric mice were crossed to C57BL/6 female mice to generate F1 wild-type ($srbI^{+/+}$) and heterozygous ($srbI+/^{+-}$) mice on an identical 129 (agouti)/C57BL/6 background. FI heterozygotes were crossed to generate F2 wild-type ($srbI^{+/+}$), heterozygous mutant ($srbI^{+/-}$) and homozygous mutant ($srbI^{+/-}$) progeny. The presence of the targeted or wild-type SR-BI alleles in DNA extracted from tail biopsies was detected by PCR amplification using primer 1 in combination with either primer 3 (mutant specific) or primer 2 (wild-type specific; 5'-TATCCTCGGCAGACCTGAGTCGTGT-3' (SEQ ID NO:7)). Genotypes were confirmed by Southern blot analysis. Mice were housed in microisolator cages and were fed ad libitum a regular rodent chow diet (Prolab 3000, PMI Feeds Inc., St. Louis, Mo.).

Analysis of animal tissues:

Samples were obtained from fasted (4–8 hrs) or non-fasted mice that were approximately 8–12 weeks old (F1 generation) or 5–11 weeks old (F2 generation).

Immunoblot Analysis.

Animals were sacrificed and livers and adrenal glands were removed and immediately frozen. Membranes from homogenates were prepared. 50 μg of protein per specimen were analyzed by SDS-polyacrylamide (8%) gel electrophoresis and immunoblotting with chemiluminescence detection as previously described using rabbit antipeptide polyclonal antibodies which specifically recognize either the approximately 82 kDa murine SR-BI protein (anti-mSR-BI[485]) or the approximately 36 kDa ε-COP control cytoplasmic protein (anti-εCOP).

Plasma and Adrenal Cholesterol Analysis.

Plasma total cholesterol (unesterified plus esterified, mg/dl) was measured using an enzymatic kit (Sigma Chemicals, St. Louis, Mo.). Adrenal glands were homogenized as described above. Protein concentrations in the homogenates were measured using the method of Lowry et al.. Duplicate samples of homogenates (30–70 μl each) were extracted with 2 ml of hexane/isopropanol (2:1) for 1 h at room temperature, back-washed with 1 ml of water, and phases separated by centrifugation at 800×g for 5 min. The upper organic phase was recovered and evaporated at 37° C. in a Speedvac concentrator and cholesterol was measured in the dried pellet using an enzymatic kit (Sigma). Cholesterol values were corrected based on the recovery of a [$^3$H] cholesteryl ester internal standard added prior to lipid extraction. Total cholesterol content was expressed as μg of cholesterol/mg total protein.

Lipoprotein Analysis.

Pooled plasma (150 μl total from 2–6 animals) was diluted with an equal volume of elution buffer (154 mM NaCl 1 mM EDTA, pH 8) and subjected to FPLC using two Superose 6 columns (Pharmacia, Piscataway, N.J.) connected in series. Proteins were eluted at 0.25 ml/min. Forty seven fractions (0.5 ml) were collected after the first 14 ml were eluted and total cholesterol in each fraction was determined as described above. Immunoblotting of the FPLC fractions was performed with specific anti-apoA-I, anti-apoA-II or anti-apoE antibodies on independent samples or by sequential labeling of a single membrane to permit simultaneous visualization of all three proteins.

Statistical Analysis.

Results are expressed as the arithmetic mean ± standard deviation. The statistical significance of the differences of the mean between groups was evaluated using the Student t test for unpaired comparisons. The $\chi^2$ test was used for genotype distribution analysis. P values <0.05 are considered to be statistically significant.

Results and Discussion

The SR-BI gene was inactivated in embryonic stem cells by standard homologous recombination methods. The segments replaced in the recombined mutant ("Targeted Allele") include the entire coding region of the first coding exon (126 bp, 42 amino acids, containing 5' untranslated sequence, a short N-terminal cytoplasmic domain, and a portion of the N-terminal putative transmembrance domain that probably also functions as an uncleaved leader sequence for insertion into the ER during biogenesis) and an additional 554 bases of the adjacent downstream intron. The mutated locus is expected to encode a transcript which would not be translated or would be translated into non-functional, non-membranous, and presumably unstable, protein. The strategy for the targeted disruption of the SR-BI locus in the mouse. Abbreviations: TK, herpes simplex thymidine kinase; neo, pol2sneobpA expression cassette, X, Xba I; B, Bam, HI; S, Sac I; "ATG", codon for the initiator methionine. Two sets of primer pairs specific for the wild-type (primers 1 and 2) or targeted mutant (primers 1 and 3) alleles were used to screen genomic DNA by PCR as described in heterozygous and F2 homozygous mutant animals are shown. Immunoblot analysis of hepatic membranes (50 μg protein/lane) from unfasted wild-type (F1 and F2 generations), heterozygous (F1 and F2 generations) and homozygous mutant (F2 generation) male mice were performed using polyclonal antipeptide antibodies to SR-BI (approximately 82 kDa, top) or the internal control ε-COP (approximately 36 kDa). Essentially identical results were obtained using specimens from female mice) confirmation of the expected null mutation by PCR.

Three independently derived embryonic stem cell clones containing the targeted allele were injected into C57BL/6 blastocysts and two produced 24 male chimeras, of which 11 gave germ line transmission of the targeted SR-BI allele when crossed to c57BL/6 females. F1 offspring were either homozygous (+/+) for the wild type allele or heterozygous (+/−) with both mutant and wild-type PCR products. F1 heterozygotes should be isogenic with the F1 wild-type controls except at the SR-BI locus. Wild-type, heterozygous and homozygous mutant F2 generation offspring, whose phenotypes are subject to genetic background variability, were generated from F1 intercrosses. In the F2 progeny analyzed to date (n=317), the observed ratios of wild-type heterozygous mutant homozygous mutant offspring were 1.0:1.7:0.5, values significantly different from the expected Mendelian ratio of 1:2:1 (p=0.003). Thus, there may be partially penetrant effects of the mutation either on neonatal survival or on embryonic development, which would be consistent with the distribution of SR-BI on the maternal surfaces of cells in the placenta and yolk sac during embryonic development.

All of the mutants looked normal (weight, general appearance and behavior) and the males were fertile. No offspring from female homozygous mutants have been obtained following multiple attempts to do so, indicating a substantial, and possibly complete, decrease in fertility in these females. Immunoblot analysis of liver membranes from F1 (+/+,+/−) and F2 (+/+,+/−,−/−) mice using anti-peptide antibodies which recognize the C-terminus of the SR-BI protein (anti-mSR-BI$^{495}$), or a segment of the putative extracellular loop (anti-mSR-BI$^{230}$), revealed that there was about half as much mSR-BI protein in the heterozygous mutants as in the wild-type controls and no detectable SR-BI in the homozygous mutants. No fragment or other variants of the full-length protein were detected in any of the samples. In contrast, no significant differences were observed in the levels of the control protein, $\epsilon$-COP. Similar results were observed using adrenal tissue. Thus, the mutated SR-BI gene is a functionally null allele.

To determine how decreased SR-BI protein expression influenced lipoprotein metabolism, the plasma cholesterol levels in male and female wild-type and mutant mice were compared. Because there were no statistically significant differences between the data from animals derived from the two independent embryonic stem cell clones, data from these two independent sets of animals were pooled. Relative to wild-type controls there were statistically significant increases in the plasma total cholesterol concentrations of approximately 30–40% in F1 and F2 heterozygotes and 2.2-fold in F2 homozygous mutants. In contrast to the increased plasma cholesterol in the mutants, there was no statistically significant change in the levels of plasma apoA-I. These findings are consistent with the suggestion that hepatic SR-BI plays a key role in selective removal of cholesterol from circulating HDL-lower levels of hepatic SR-BI were expected to increase plasma HDL cholesterol but not directly alter apoA-I levels.

To determine if the elevated levels of plasma cholesterol in the mutants were due to changes in HDL, pooled plasma samples from F1 male and female and F2 male animals were subjected to FPLC and the total cholesterol content as well as the relative amounts of apoA-I, apoA-II and apoE in each fraction were measured. For wild-type mice (srbI$^{+/+}$) most of the cholesterol, apoA-I and apoA-II were in the HDL fraction, with small or undetectable amounts in the VLDL and IDL/LDL fractions. There was an apparently low level of apoE which both co-migrated with the HDL and with a small cholesterol peak in the IDL/LDL region. The cholesterol and apolipoprotein profiles of the heterozygous mutants were similar to those of the wild-type controls, except that there was an increase in the amount of cholesterol in the HDL fractions and there was a tendency of the HDL peak (cholesterol and/or apolipoproteins) to be broader than that of wild-type and shifted slightly to the left, which may represent large HDL particles. This suggested that there might be a difference in the average sizes of the HDL particles due to the inactivation of one of the SR-BI alleles; however, this shift was not observed in all specimens. In the F2 homozygous mutant animals (srbI$^{-/-}$) the cholesterol was found in a large, somewhat heterogeneous peak in the HDL range, but shifted to the left (larger apparent size) of the wild-type HDL peak. The amount of cholesterol in the IDL/LDL fraction varied between samples.

Combined immunoblot analysis of fractions 23–28 from the chromatograms were performed with polyclonal antibodies to apoE, apoA-I and apoAII. Additional analysis of these and independent chromatograms established that there were no additional peaks containing apoA-I in fractions containing larger lipoproteins (fractions 1–22) and that the only other peak containing a small amount of apoE was in fraction 6, which corresponds to VLDL. The distributions of apoA-I and apoA-II were similar to that of cholesterol, although, unlike the case for apoA-I there was a notable reduction in the amount of apoA-II relative to that seen in wild type and heterozygous mutant animals. Conversely, in the homozygous mutants there was a substantial increase in the amount of apoE, whose distribution profile (larger particles, centered around fractions 26–28) differed from, but overlapped, those of apoA-I and apoA-II.

These results with the mutant animals, in which the changes in SR-BI expression are in the physiologic range, are complementary to and consistent with the observation that transient adenovirus-mediated hepatic SR-BI overexpression results in dramatically decreased levels of HDL cholesterol and increased delivery of HDL-associated lipid to hepatocytes and the bile. In rodents, most of the plasma HDL cholesterol appears to be removed by the liver via selective uptake and the liver appears to be the site of the highest total amount of SR-BI protein expression. It seems likely that buildup of large, cholesterol-enriched lipoprotein particles in the circulation of SR-BI mutants was primarily due to decreased hepatic selective HDL cholesterol uptake. Thus, it appears that murine plasma HDL cholesterol levels are particularly sensitive to physiologically relevant changes in the levels of hepatic SR-BI protein expression (e.g., approximately 50% reduction in heterozygotes). The effect of the null mutation in SR-BI on total plasma cholesterol levels was quantitatively similar to that of a null mutation in the LDL receptor. For both sets of mutants, total plasma cholesterol levels were approximately 36% above wild-type controls for heterozygotes and approximately 114% for homozygotes. It is important to emphasize that while the magnitudes of the effects on total plasma cholesterol of these distinct mutations (SR-BI vs. LDL receptor) are similar, the mechanistic consequences on lipoprotein metabolism (e.g., effects on the various lipoproteins) differ.

In addition to playing an important role in regulating plasma HDL cholesterol, SR-BI has been implicated in the delivery of HDL cholesterol to the adrenal gland and other steroidogenic tissues, both for the accumulation of esterified cholesterol stores and for steroid hormone synthesis. To examine this, the cholesterol content of adrenal glands in mutant and wild-type mice was measured. The results are shown in Table 1. As predicted, cholesterol stores in the adrenal gland dropped substantially in the heterozygous and homozygous mutants to 58% and 28% of control, respectively. It was also noted that the color of intact adrenal glands from homozygous mutants was brownish-red while that of wild-type and heterozygous animals was light yellow and, in preliminary studies, a dramatic decrease in oil red O staining of the adrenal cortex was observed in the homozygous mutants relative to the wild-type mice. Thus, the total cholesterol content, color and oil red O staining characteristics of the adrenal glands in SR-BI homozygous mutants resembled those in their cholesterol-depleted counterparts in other murine mutants, including null mutants in the SR-BI ligand apoA-I. This similarity with apoA-I knockouts is consistent with the possibility that the reduction in adrenal cholesterol in the SR-BI homozygotes is a direct consequence of the loss of the key receptor for selective lipid uptake. Recent antibody blocking experiments have provided additional support for a major role of mSR-BI in delivering HDL cholesterol to cultured adrenocortical cells for steroidogenesis. Based on the tissue distribution and hormonal regulation of SR-BI protein expression and the phenotypes of apoA-I knockouts, it seems likely that there would also be reductions in cholesterol stores in other steroidogenic tissues (e.g., ovary, testes) in SR-BI homozygous mutants. Adrenal cholesterol deficiency in both the apoA-I and SR-BI homozygous mutants also suggests that LDL receptors in the mouse, in which there normally is little LDL in the plasma, do not normally contribute significantly to murine adrenal cholesterol accumulation.

animals died as the result of progressive heart block (major cardiac conduction defects), as revealed by changes in electrocardiograms and extensive cardiac fibrosis. These were accompanied by coronary artery atherosclerosis. Complete occlusion of coronary arteries with a lipid-poor material which appears to represent the formation of occlusive fibrin/platelet clots, strongly suggests that the mice die of myocardial infarctions due to atherosclerosis/thrombosis, just like humans.

These animals should prove useful as a model for human coronary artery disease and myocardial infarctions, and probably stroke. This animal system should prove to be amenable to the rapid testing of potential drugs (since the mice succumb to MI's very rapidly—within weeks). These results also suggest that under certain circumstances, manipulation of mice deficient in either SR-BI or apo E alone (for example interventions to alter lipoprotein metabolism, altered steroidogenesis etc) might give rise to similarly severe coronary artery disease and myocardial infarctions, giving rise to equally useful models of human coronary artery disease.

The HDL receptor SR-BI mediates the selective uptake of plasma HDL cholesterol by the liver and steroidogenic tissues. As a consequence, SR-BI can influence plasma HDL cholesterol levels, HDL structure, biliary cholesterol

TABLE 1

EFFECTS OF DISRUPTION OF THE GENE ENCODING SR-BI ON PLASMA TOTAL CHOLESTEROL AND APO A-I CONCENTRATIONS, AND ADRENAL GLAND TOTAL CHOLESTEROL CONTENT IN WILD-TYPE (srbI$^{+/+}$), AND HETEROZYGOUS (srbI$^{+/-}$), AND HOMOZYGOUS (srbI$^{-/-}$) MUTANT MICE.

| | | F1 Generation | | F2 Generation$^\S$ | | | | | |
|---|---|---|---|---|---|---|---|---|---|
| | | Plasma Total Cholesterol | | Plasma Total Cholesterol | | Plasma ApoA-I | | Adrenal Gland Total Cholesterol | |
| srbI genotype | gender | mg/dl | % of control | mg/dl | % of control | mg/dl | % of control | µ/mg protein | % of control |
| +/+ | male | 93 ± 8 (29) | 100 | 99 ± 12 (18) | 100 | — | — | — | — |
| | female | 80 ± 7 (13) | 100 | 94 ± 20 (27) | 100 | — | — | — | — |
| | Both | 89 ± 10 (42) | 100 | 96 ± 17 (45) | 100 | 25 ± 3 (10) | 100 | 128 ± 28 (5) | 100 |
| +/− | male | 126 ± 10 (21) | 100 | 137 ± 21 (29) | 100 | — | — | — | — |
| | female | 112 ± 9 (23) | 140 | 118 ± 9 (49) | 112 | — | — | — | — |
| | Both | 126 ± 12 (44) | 134 | 126 ± 22 (78) | 131 | 28 ± 2 (12) | 112 | 74 ± 18 (6) | 58 |
| −/− | male | — | — | 220 ± 41 (10) | 222 | — | — | — | — |
| | female | — | — | 209 ± 32 (7) | 222 | — | — | — | — |
| | Both | — | — | 216 ± 37 (17) | 225 | 27 ± 3 (11) | | 36 ± 7 (5) | 28 |

Values for F1 generation represent mean ± standard deviation. Values for F2 generation in parenthesis represent the numbers of animals analyzed.
Values for plasma total cholesterol determined with an Autoanalyzer and human apoA-I standards.
F1 generation animals were not fasted. F2 generation animals were not fasted prior to analysis of adrenal gland cholesterol levels but were fasted for 4–8 h prior to analysis of plasma.

EXAMPLE 2

SR-BI/Apo E Double Knockout Mice

To study the effects of a lack of expression of the gene encoding the Scavenger Receptor, class B type I (SR-BI) on atherosclerosis, mice deficient in SR-BI (SR-BI KO mice) were crossed to mice deficient in apolipoprotein E (apo E KO mice). Mice deficient in both SR-BI and apo E (SR-BI/apo E double KO mice) did not survive beyond 8–9 weeks of age. Analysis of atherosclerosis in these mice revealed extensive atherosclerotic plaque in the aortic sinuses of SR-BI/apo E double KO mice at 5–7 weeks of age, at which time, no atherosclerotic plaque formation was detectable in mice deficient in either SR-BI or apo E alone. Further analysis of SR-BI/apo E double KO mice revealed that the concentrations, and the uptake, storage and utilization of cholesterol by steroid hormone producing cells. Here we used homozygous null SR-BI knockout mice to show that SR-BI is required for maintaining normal biliary cholesterol levels, oocyte development and female fertility. We also used SR-BI/apoE double homozygous knockout mice to show that SR-BI can protect against early onset atherosclerosis. Although the mechanisms underlying the effects of SR-BI loss on reproduction and atherosclerosis have not been established, potential causes include changes in: i) plasma lipoprotein levels and/or structure, ii) cholesterol flux into or out of peripheral tissues (ovary, aortic wall), and iii) reverse cholesterol transport, as indicated by the significant reduction of gallbladder bile cholesterol levels in SR-BI and SR-BI/apoE double knockout mice relative to controls.

If SR-BI has similar activities in humans, it may become an attractive target for therapeutic intervention in a variety of diseases.

INTRODUCTION

High density lipoprotein (HDL)-cholesterol levels are inversely proportional to the risk for atherosclerosis Gordon et al., *N. Engl. J. Med.* 321, 1311–1316 (1989). This may partly be due to "reverse cholesterol transport" (RCT), in which HDL is proposed to remove excess cholesterol from cells, including those in the artery wall Johnson, et al., *Biochim. Biophys. Acta*, 1085, 273–298 (1991), Tall, A.R. *J. Lipid Res.* 34, 1255–1274 (1993), Pieters, et al., *Biochim. Biophys. Acta* 1225, 125–134 (1994), Fielding, et al., *J. Lipid. Res.* 36, 211–228 (1995), Oram, et al., *J. Lipid Res.* 37, 2473–2491 (1996), Breslow, J.L. In *The Metabolic and Molecular Bases of Inherited Diseases*. eds. Scriver, C.R., Beaudet, A.L., Sly, W.S., & Valle, D. (McGraw-Hill, New York), pp. 2031–2052 (1995), and transport it, either indirectly or directly Glass, et al., *Proc. Natl. Acad. Sci. USA* 80, 5435–5439 (1983) and Glass, et al., *J. Biol. Chem.* 260, 744–750 (1985), to the liver for biliary secretion. HDL can also directly deliver cholesterol to steroidogenic tissues (adrenal gland, testis, ovary) for storage in cytoplasmic cholesteryl ester droplets and for steroid hormone synthesis, Gwynne, et al., *Endocr. Rev.* 3, 299–329 (1982), Kovanen, et al., *J. Biol. Chem.* 254, 5498–5505 (1979), and Plump, et al., *J. Clin. Invest.* 97, 2660–2671 (1996). Thus, HDL may influence a variety of endocrine functions, including reproduction. A key mechanism of receptor-mediated direct delivery of HDL cholesteryl esters to the liver and steroidogenic tissues is selective cholesterol uptake, in which only the cholesteryl esters of the HDL particles (not the apolipoproteins) are efficiently transferred to cells, Glass, et al., (1983), and Glass, et al., (1985).

The class B type I scavenger receptor, SR-BI, is a cell surface HDL receptor which mediates selective lipid uptake, Acton, et al., *Science* 271, 518–520 (1996), Babitt, et al., *J. Biol. Chem.* 272, 13242–13249 (1997), Gu, et al., *J. Biol. Chem.* 273, 26338–26348 (1998), Temel, R.E., et al., *Proc. Natl. Acad. Sci. USA.* 94, 13600–13605 (1997), Kozarsky, K.F., et al., *Nature* 387, 414–417 (1997), Rigotti A., et al., *Proc. Natl. Acad. Sci. USA.* 94, 12610–12615 (1997), Varban, M.L. et al.,. *Proc. Natl. Acad. Sci. USA.* 95, 4619–4624 (1998), Wang, N., et al., *J. Biol. Chem.* 273, 32920–32926 (1998), Ueda, Y., et al., *J. Biol. Chem.* 274, 7165–7171 (1999), reviewed in Rigotti, A., et al., *Curr. Opin. Lipidol.* 8, 181–188 (1997), and Krieger, M *Ann. Rev. Biochem.* 68, 523–558 (1999). It is most highly expressed in the liver and steroidogenic tissues, in which its activity is regulated by trophic hormones, Acton, (1996), Rigotti, A., et al., *J. Biol. Chem.* 271, 33545–33549 (1996), Wang, N., et al., *J. Biol. Chem.* 271, 21001–21004 (1996), Landschulz, K.T., et al.,*J. Clin. Invest.* 98, 984–995 (1996), Mizutani, T., et al., *Biochem. Biophys. Res. Commun.* 234, 499–505 (1997), Li, X., et al.,*Endocrinology* 139, 3043–3049 (1998), Reaven, E., et al., *Endocrinology* 139, 2847–2856 (1998), Rajapaksha, W.R., et al., *Mol. Cell. Endocrinol.* 134, 59–67 (1997), and Azhar, S., et al., *J. Lipid Res.* 39, 1616–1628 (1998). As a consequence, SR-BI is a key regulator of HDL cholesterol levels, Kozarsky, (1997), Rigotti A., et al., (1997), Varban, M.L. et al., (1998), Wang, N., et al., (1998), and Ueda, Y., et al., (1999), and adrenal cholesterol stores, Rigotti A., et al., (1997). The finding that hepatic SR-BI overexpression leads to significant increases in biliary cholesterol content, Kozarsky, K.F., et al., (1997), and Sehayek, E., et al., *Proc. Natl. Acad. Sci. USA.* 95, 10194–10199 (1998), is consistent with gene targeting studies Rigotti A., et al., (1997), and Varban, M.L. et al., (1998), which suggest an important role for SR-BI in RCT. In addition to HDL, SR-BI can bind other ligands, including lipoproteins (LDL, modified LDL, VLDL) and apolipoproteins, Acton, S.L., et al., *J. Biol. Chem.* 269, 21003–21009 (1994), Murao, K., et al., *J. Biol. Chem.* 272, 17551–17557 (1997), Calvo, D., et al.. *Arterioscler. Thromb. Vasc. Biol.* 17, 2341–2349 (1997), Rigotti, A., et al.,*J. Biol. Chem.* 270, 16221–16224 (1995), Xu, S., et al., *J. Lipid Res.* 38, 1289–1298 (1997), and can mediate efflux of unesterified cholesterol from cells to HDL, Ji, Y., et al., *J. Biol. Chem.* 272, 20982–20985 (1997), and Stangl, H., et al., *J. Biol. Chem.* 273, 31002–31008 (1998).

Because inactivation of SR-BI is associated with both decreased RCT, Rigotti A., et al., (1997), and Varban, M.L. et al., (1998), and increased plasma HDL cholesterol (albeit in abnormally large particles containing apolipoproteins AI (apoA-I) and E (apoe) Rigotti A., et al., (1997), a key question has arisen: Do decreases in SR-BI expression inhibit or promote atherosclerosis? Here we addressed this question by studying crosses between apoE KO mice, which on a chow diet spontaneously develop atherosclerosis at around 3 months of age, Zhang, S.H., et al., *Science* 258, 468–471 (1992), Zhang, S.H., et al., *J. Clin. Invest.* 94, 937–945 (1994), and Plump, A.S., et al., *Cell* 71, 343–353 (1992), and SR-BI KO mice. The results clearly show that genetically suppressing SR-BI activity in apoE KO mice dramatically accelerates the onset of atherosclerosis. We also report that female mice deficient in SR-BI alone are infertile, apparently due in part to abnormalities in the viability and developmental potential of their oocytes. Thus, genetic ablation of SR-BI has profound effects on both cardiovascular and reproductive pathophysiology in mice.

MATERIALS AND METHODS

Animals

Mice (mixed C57BL/6×129 background) were housed and fed a normal chow diet as described in Rigotti A., et al., (1997). SR-BI$^{-/-}$ mice Rigotti A., (1997), and apoE$^{-/-}$ mice (The Jackson Laboratory, Zhang, S.H., et al., (1992), and Zhang, S.H., et al., (1994)), were mated and the double heterozygous offspring were intercrossed. The resulting SR-BI$^{+/-}$ ApoE$^{-/-}$ offspring were mated to produce single apoE KO and double SR-BI/apoE KO animals. Genotypes were determined by PCR analysis (Rigotti A., et al., (1997), also see The Jackson Laboratory web site). Estrus cycles were followed by vaginal cytology, Nelson, J.F., et al., *Biol. Reprod.* 27, 327–339 (1982), and external appearance, Hogan, B., et al., *Manipulating the Mouse Genome* (Cold Spring Harbor Laboratory Press, Plainview, N.Y.) Second edition. p. 129–191 (1994). Superovulation was induced by intraperitoneal injection of 5 IU each of pregnant mare's serum (Calbiochem) and human chorionic gonadotropin (Organon) as described in Hogan, B., et al., (1994). Pseudopregnancy was induced by mating (confirmed by detection of vaginal seminal plug) with vasectomized males (Taconic) Hogan, B., et al., (1994). Ovaries were harvested and prepared for sectioning as described below, and oocytes and preimplantation embryos were harvested as described Hogan, B., et al., (1994) and cultured in KSOM medium with amino acids (Specialty Media).

Plasma and bile analysis

Blood was collected in a heparinized syringe by cardiac puncture from mice fasted overnight. Plasma was subjected to FPLC analysis, Rigotti A., et al., (1997), either immediately after isolation or after storage at 4° C. Total cholesterol was assayed as described in Rigotti A., et al., (1997).

Cholesterol from non-apoB containing lipoproteins was determined either using the EZ HDL kit (Sigma, based on an antibody which blocks detection of cholesterol in non-HDL lipoproteins, and validated by us using human or mouse lipoproteins, not shown) or after precipitation with magnesium/dextran sulfate (Sigma; Zhang, S.H., et al., (1992), and Plump, A.S., et al., *J. Lipid Res.* 38, 1033–1047 (1997). Plasma (0.4 μl) and FPLC fractions or pools were analyzed by SDS-polyacrylamide, Rigotti A., et al., (1997), or agarose gel electrophoresis, Fielding, C.J. et al., *Methods Enzymol.* 263, 251–259 (1996), and immunoblotting, Towbin, H., et al., *Proc. Natl. Acad. Sci. USA* 76, 4350–4354 (1979), and Ishida, B.Y., et al., *J. Lipid Res.* 31, 227–236 (1990), with chemiluminescence detection as previously described Rigotti A., et al., (1997), using primary anti-apolipoprotein antibodies (Sigma, or gifts from J. Herz and H. Hobbs) and corresponding horseradish peroxidase coupled secondary antibodies (Jackson Immuno Research or Amersham). The Attophos chemifluorescence kit (Amersham) and an alkaline phosphatase coupled goat anti-rabbit secondary antibody (gift from D. Housman) were used with a Storm Fluorimager (Molecular Dynamics) for quantitative analysis. Plasma progesterone concentrations were determined by radioimmunoassay (Diagnostics Products Corp, Los Angeles, Calif.). Cholesterol was extracted from gallbladder bile and assayed as described in Puglielli, L., et al., *Biochem. J.* 317, 681–687 (1996).

Histology and immunofluorescence microscopy

Mice anesthetized with 2.5% avertin were perfused through the left ventricle with 20 ml of ice cold PBS containing 5 mM EDTA. Hearts were collected directly, or the mice were perfused (5 ml) with paraformaldehyde and the hearts collected and treated as described Bourassa, P.-A.K. et al., *J. Histotechnology* 21, 33–38 (1998). Hearts and ovaries were frozen in Tissue Tek OCT (Sakura, Torrance, Calif.). Serial cross sections (10 μm thickness through aortic sinuses Zhang, S.H., et al., (1994), Paigen, B., et al., *Atherosclerosis* 68, 231–240 (1987), and Suzuki, H. et al., *Nature* 386, 292–296 (1997), 5 μm for ovaries, Reichert-Jung cryostat) were stained with oil red O and Meyer's hematoxylin, R.E. Coalson in *Staining Procedures*, G. Clark, Ed. (Williams and Wilkins, Baltimore) pp 217–253 (1981). Images were captured for morphometric analysis using a computer assisted microscopy imaging system and lesion size was quantified as the sum of the cross-sectional areas of each oil red O staining atherosclerotic plaque in a section Paigen, B., et al., (1987), using NIH Image software. Immunohistochemistry with a monoclonal anti-α smooth muscle actin antibody (Sigma, gift from R. Hynes) was performed as described in Rigotti, A., et al., (1996). Cumulus/oocyte complexes, isolated from the oviducts of superovulated females as described in Hogan, B., et al., (1994), or denuded oocytes (zona pellucida removed as in Hogan, B., et al., (1994)) were immunostained with polyclonal rabbit anti-murine SR-BI antibodies (Acton, et al., (1996), or a gift from K. Kozarsky) and Cy3-labeled donkey anti-rabbit secondary antibodies (gift from R. Rosenberg) as described in Babitt, et al., (1997) and Hatzapoulos A.K., et al., *J. Lipid Res.* 39, 495–508 (1998).

Statistical Analysis

Data were analyzed using either a two-tailed, unpaired Student t-test (total or EZ HDL cholesterol from plasma, bile or FPLC fractions, progesterone and apoA-I levels) or an unpaired nonparametric Kruskall-Wallis test (atherosclerotic plaque lesion sizes) (Statview and Microsoft Excel). Values are presented as means ± standard deviations.

RESULTS AND DISCUSSION

Reproductive Pathophysiology

Homozygous SR-BI knockout (KO) males exhibit normal fertility, Rigotti A., et al., (1997). In contrast, homozygous KO females are infertile. In a two month pairing of either homozygous KO or heterozygous females with homozygous SR-BI KO males (n=8 for each), heterozygous females produced 19 litters and 82 healthy offspring, whereas the homozygous females produced no healthy offspring. Although two pups from two homozygous SR-BI KO females were born, they died soon after.

There were no obvious gross morphological abnormalities in SR-BI KO ovaries. Six week old female mice were superovulated and were mated to males of the other genotype (i.e., SR-BI$^{+/+}$ females mated to SR-BI$^{-/-}$ males and vice versa) to generate embryos with heterozygous mutant genotypes. Ovaries and preimplantation embryos were harvested the following morning (day 0). Typical oil red O staining of lipids in ovaries from SR-BI$^{+/+}$ or SR-BI$^{-/-}$ animals was performed. Phase contrast microscopy of pre-implantation embryos (cultured for one day) from SR-BI$^{+/+}$ or SR-BI$^{-/-}$ females mated to males of the opposite genotype was also performed. Similar results were observed when SR-BI$^{-/-}$ males were mated to SR-BI$^{-/-}$ females. Plasma progesterone concentrations from pseudopregnant females (6 days postmating, age 6–10 weeks, weight 19–25 g, n=8.) (P=0.08). Percent of preimplantation embryos from SR-BI$^{+/+}$ or SR-BI$^{-/-}$ females with normal morphology during 3 days of culture were calculated. The values represent the averages from 5 animals of each genotype. Total number of embryos: SR-BI$^{+/+}$, 131; SR-BI$^{-/-}$, 167. Histochemical analysis of ovaries from superovulated females showed reduced oil red O-staining of lipids in the ovarian corpora lutea of SR-BI KO relative to those of wild-type animals. This suggests there was reduced cholesteryl ester storage, as previously observed in adrenal glands from SR-BI KO mice Rigotti A., et al., (1997). This raised the possibility that there might have been insufficient amounts of cholesterol substrate in the corpora lutea to sustain adequate steroid hormone production for pregnancy. However, plasma progesterone levels between pseudopregnant control and KO females 6 days after mating, either without or with superovulation were not significantly different. Furthermore, several other murine homozygous knockout mutants (e.g. LCAT, ACAT, and apoA-I) exhibit similar lipid depletion in steroidogenic tissues Plump, et al., (1996), Meiner, V.L., et al., *Proc. Natl. Acad. Sci. USA* 93, 14041–14046 (1996), and Ng, D.S., et al., *J. Biol. Chem.* 272, 15777–15781 (1997), without apparent female infertility. Thus, normal lipid stores are not required for synthesis of adequate amounts of steroid hormones for female fertility.

Although KO females were infertile, they exhibited no obvious defects in their estrus cycles or numbers of oocytes ovulated, either during normal estrus or after superovulation (wild type (n=4), 52±5 oocytes; SR-BI KO (n=3), 41±8, P=0.2). Because the estrus cycle and ovulation depend on estrogen (e.g., for follicular development and induction of LH receptors) and progesterone (e.g., for follicular rupture), Elvin, J.A. et al., *Reviews of Reproduction* 3, 183–195 (1998), KO females apparently synthesize adequate levels of intra- and extraovarian steroids for at least some, if not all, ovarian functions.

Because the extent of ovulation by the KO mice appeared normal, we compared the viability and development of heterozygous (SR-BI$^{+/-}$) preimplantation (1-cell) embryos placed into culture the morning (day 0) after mating with males. Almost all embryos from wild-type females had normal morphologies and developed into morulas or blastocysts after 3 days in culture. In contrast, the majority of embryos from KO females at harvesting had an abnormal, non-refractile morphology, reminiscent of that seen in embryos mechanically damaged during pronuclear injection, Hogan, B., et al., (1994). The abnormal (presumably dead) embryos did not develop further. All of the other embryos from SR-BI KO females which appeared normal on day 0 eventually adopted the abnormal morphology and arrested (most at the 1- or 2- cell stages) in culture. We also observed a similar abnormal morphology in oocytes from wild-type females that had been treated in culture with 50 µg/ml of nystatin or filipin, cholesterol binding drugs which can perturb membrane structure, Bolard J. *Biochim. Biophys. Acta* 864, 257–304 (1986).

The same abnormal morphology was seen in newly harvested unfertilized oocytes from SR-BI KO (n=6), but not wild-type (n=7), superovulated females, although at a lower frequency (31±22%) than in fertilized preimplantation embryos (69±19%, P=0.02). Therefore, some of the oocyte abnormalities apparently are fertilization and cell division independent. Using immunostaining with anti-SR-BI antibodies, we did not detect a signal for SR-BI in wild-type oocytes, either denuded (zona pellucida removed) or in cumulus complexes, above the background seen in oocytes from KO animals, suggesting that after ovulation murine oocytes do not express high levels of SR-BI (also see Reaven, E., et al., (1998)). In contrast, substantial expression of SR-BI was detected in the expanded cumulus cells surrounding ovulated oocytes from wild-type, but not SR-BI KO, mice. These cells are derived from follicular granulosa cells and are believed to play a key role in oocyte development, Meiner, V.L., et al., (1996). SR-BI expression has been reported to be induced in follicular granulosa cells soon after a luteinizing pulse of human chorionic gonadotropin Mizutani, T., et al., (1997), Li, X., et al., (1998), Reaven, E., et al., (1998), and Rajapaksha, W.R., et al., (1997).

Infertility in SR-BI KO females may be due to inadequate delivery of HDL-cholesterol for membrane synthesis or steroidogenesis, inadequate delivery of non-steroidal HDL lipids (e.g., lipid soluble vitamins), or deficiencies in SR-BI functions other than selective cholesterol uptake (lipid efflux, binding of non-HDL ligands). The abnormal structure of plasma HDL in the KO animals (large, apoE-rich, Rigotti A., et al., (1997)) may also contribute to the infertility. Oocyte abnormalities may arise due to the inability of cumulus cells to express SR-BI, before or after ovulation, because SR-BI may be needed by these cells to properly nourish the oocyte and/or support its development. SR-BI expression may also be needed in ovarian interstitial and thecal cells surrounding follicles Landschulz, K.T., et al., (1996), Mizutani, T., et al., (1997), Li, X., et al., (1998), and Reaven, E., et al., (1998). during oocyte maturation or in the oviduct environment (at least up to the one-cell stage). SR-BI might also play a role at other stages of reproduction and development. For example, the pattern of expression of SR-BI during later stages of pregnancy Hatzapoulos A.K., et al., (1998), and Wyne, K.L. et al., *J. Lipid. Res.* 39, 518–530 (1998), and the non-Mendelian (reduced) yield of homozygous mutant offspring from heterozygous mothers, Rigotti A., et al., (1997), suggest it participates in the normal function of the decidua, yolk sac and/or placenta for nutrient transport and steroid hormone synthesis. Although additional mechanistic studies are necessary, the current data unequivocally establish that SR-BI is important for normal oocyte maturation, embryonic development and female fertility in mice.

Cardiovascular Pathophysiology

To analyze the effects of SR-BI on atherosclerosis, we crossed SR-BI KO and apoe KO (spontaneously atherosclerotic, Zhang, S.H., et al., (1992), Zhang, S.H., et al., (1994), and Plump, A.S., et al., (1992)), mice and compared the lipoprotein profiles and development of atherosclerosis in the single and double homozygous KO females at 4–7 weeks of age. Results for males were similar, except as noted. As reported in example 1, plasma total cholesterol in the single SR-BI KOs was increased relative to controls, because of an increase in large, apoE-enriched HDL particles, Rigotti A., et al., (1997), while the even greater relative plasma cholesterol increase in the single apoE KOs was a consequence of a dramatic increase in cholesterol in VLDL and IDL/LDL size particles. There was increased plasma cholesterol in the double KOs relative to the single apoE KOs, mainly in VLDL size particles. This might have occurred if SR-BI, which can bind apoB containing lipoproteins, Acton, S.L., et al., (1994), Murao, K., et al., (1997), Calvo, D., et al., (1997), directly or indirectly contributes to the clearance of the cholesterol in VLDL size particles in single apoE KO mice (reduced clearance in its absence), Wang, N., et al., (1998), and Ueda, Y., et al., (1999).

The normal size HDL cholesterol peak seen in the single apoE KOs virtually disappeared in the double KOs. However, no statistically significant differences (P=0.1) in plasma levels of HDL's major apolipoprotein, apoA-I, were detected. Based on the analysis of lipoproteins in the single SR-BI KO mice Rigotti A., et al., (1997), abnormally large HDL-like particles were expected to appear in the double KOs. Indeed, the loss of normal sized HDL cholesterol and apoA-I in the double KOs was accompanied by a shift of the apoA-I into the VLDL and IDL/LDL size fractions. Furthermore, analysis of HDL-like cholesterol in the FPLC fractions using the EZ HDL assay provides evidence for the presence of abnormally large HDL-like particles in the double KO mice. In the single apoE KO males, most of this cholesterol was in particles with the size of normal HDL, while in their double KO counterparts almost all of this cholesterol was in abnormally large particles. In addition, there was ~3.7-fold more of this HDL-like cholesterol in the double (133±24 mg/dl) than in the single (36±16 mg/dl, P=0.005) KO mice. These increases in the amounts and sizes of HDL-like cholesterol by inactivation of the SR-BI gene in an apoE KO background were reminiscent of those seen in a wild-type background (~2.2-fold increase in cholesterol Rigotti A., et al., (1997), although the HDL-like particles in the double KO mice were much larger and more heterogeneous than those in the SR-BI single KO mice Rigotti A., et al., (1997). A similar trend was seen for female mice, except that there were increased levels of abnormally large HDL-like cholesterol in the single apoE KO females relative to males. Preliminary cholesterol measurements using magnesium/dextran sulfate precipitation of lipoproteins (40, 45) support the EZ HDL findings of large HDL in the double KO animals.

Additional evidence for abnormally large HDL-like particles in the IDL/LDL size range from both males and females was obtained using agarose gel electrophoresis and immunoblotting. There was a significant reduction in the amount of immunodetectable apoB present in the IDL/LDL-sized particles from the double KOs relative to the single apoe KOs, even though there was as much or more total cholesterol in these fractions in the double KOs. In addition, there was significantly greater heterogeneity in the electrophoretic mobilities of apoA-I containing IDL/LDL-sized particles. This was in part due to the presence of novel apoA-I containing, apoB-free, HDL-like particles. In contrast, most of the apoA-I in the single apoE KOs appeared to comigrate with apoB. Thus, it appears that normal size HDL in the single apoe KO animals was replaced by very large (VLDL/IDLILDL-size) HDL-like particles in the double KO animals. It is possible that normal size HDL is converted into these large HDL-like particles in the absence of both apoE and SR-BI because of substantially reduced selective (SR-BI mediated) and apoE-mediated uptake or transfer of cholesterol from HDL particles.

In addition to examining plasma cholesterol, we measured biliary cholesterol in the mice. Cholesterol levels in gallbladder bile were significantly reduced in SR-BI single KO (30%, P<0.005) and SR-BI/apoE double KO (47%, P<0.0005) mice relative to their SR-BI$^{+/+}$ controls. This is consistent with the previous finding that hepatic overexpression of SR-BI increases biliary cholesterol levels Kozarsky, K.F., et al., (1997) and Sehayek, E., et al., (1998), and indicates that SR-BI may normally play an important role in the last stage of reverse cholesterol transport-transfer of plasma HDL cholesterol into bile. The data also suggest that apoE expression can regulate biliary cholesterol content in a SR-BI KO, but not SR-BI$^{+/+}$, background.

Atherosclerosis in the animals was assessed by analyzing plaque areas in aortic sinuses and the effects of SR-BI gene disruption on plasma lipoproteins in apoE KO mice. Mice were 4–7 weeks old. Plasma apoA-I levels (right, mean±SD, expressed as relative units) were determined by SDS-polyacrylamide (15%) gel electrophoresis followed by quantitative immunoblotting for apoE$^{-/-}$ (n=7) and SR-BI$^{-/-}$ apoE$^{-/-}$ females (n=5) (P=0.1). Lipoprotein cholesterol profiles: Plasma lipoproteins from individual apoE$^{-/-}$ or SR-BI$^{-/-}$ apoE$^{-/-}$ females were separated based on size (Superose 6-FPLC) and total cholesterol in each fraction (expressed as mg/dl of plasma) was measured. Pooled Superose 6-FPLC fractions (~21 µl per pool) from females in an independent experiment were analyzed by SDS-polyacrylamide gradient (3–15%) gel electrophoresis and immunoblotting with an anti-apoA-I antibody, Rigotti A., et al., (1997). Each pool contained 3 fractions and lanes are labeled with the number of the middle fraction in each pool. Average EZ HDL cholesterol FPLC profiles for apoE$^{-/-}$ or SR-BI$^{-/-}$ apoE$^{-/-}$ males (n=3) or females (n=3). Agarose gel electrophoresis and immunoblotting: Pooled fractions (Kovanen, et al., (1979), Plump, et al., (1996), Acton, et al., (1996), Babitt, et al., (1997), Gu, et al., (1998), Temel, R.E., et al., (1997), Kozarsky, K.F., et al., (1997), Rigotti A., et al., (1997), Varban, M.L. et al., (1998), Wang, N., et al., (1998), and Ueda, Y., et al., (1999),, 3.5 µl) from the IDL/LDL region of the lipoprotein profile from individual apoE$^{-/-}$ or SR-BI$^{-/-}$ apoE$^{-/-}$ females were analyzed using either anti-apoA-I or anti-apoB antibodies. Migration was upward from negative to positive. Gallbladder biliary cholesterol (mean±SD): Total gallbladder biliary cholesterol from both male and female mice of the indicated genotypes (n=10 or 11 per genotype) was measured. Except for the wild-type and apoE$^{-/-}$values, all pairwise differences were statistically significant (P<0.025–0.0005).

To determine the effects of SR-BI gene disruption on atherosclerosis in apoe KO mice. Atherosclerosis in SR-BI$^{-/-}$ (n=8, 4–6 weeks old), apoE$^{-/-}$ (n=8, 5–7 weeks old), or SR-BI$^{-/-}$ apoE$^{-/-}$ (n=7, 5–6 weeks old) female mice was analyzed in cryosections of aortic sinuses stained with oil red O and Meyer's hematoxylin as described in Methods. Representative sections through the aortic root region and cross-sectional areas of oil red O stained lesions in the aortic root region, showed average lesion areas (mm$^2$±SD) for SR-BI$^{-/-}$ apoE$^{-/-}$, apoE$^{-/-}$ or SR-BI$^{-/-}$ mice, respectively, were as follows 0.10±0.07, 0.002±0.002, and 0.001±0.002 (P=0.0005). Also see Table II. High magnification views of serial sections of plaque from the aortic sinus of a 7 week old SR-BI/apoE double KO male, stained either with oil red O and Meyer's hematoxylin or with an anti-α actin antibody which recognizes smooth muscle cells. The lumen is to the left of the plaque. The smooth muscle wall and cellular cap are indicated. (Table II quantitative analysis of females; qualitative analysis of a smaller sample of males gave similar results. There were virtually no detectable lesions in the single KO animals at this relatively young age (4–7 weeks, Zhang, S.H., et al., (1992), Zhang, S.H., et al., (1994), Plump, A.S., et al., (1992). However, there was substantial, statistically significant, lesion development in the double KOs in the aortic root region, elsewhere in the aortic sinus (Table 11), and in coronary arteries. The lipid-rich lesions were cellular (hematoxylin stained nuclei were seen at high magnification) and in some cases had a cellular cap which stained with antibodies to smooth muscle actin. Thus, the atherosclerotic plaques were relatively advanced.

Potential causes of the dramatically accelerated atherosclerosis in the double KOs include: i) changes in relative amounts of cholesterol in proatherogenic (e.g., increased VLDL sized or abnormally large HDL-like particles) and antiatherogenic (e.g., loss of normal HDL) lipoproteins, ii) altered flux of cholesterol into or out of the aortic wall, perhaps directly due to SR-BI-mediated efflux, Kozarsky, K.F., et al., (1997), Ji, Y., et al., (1997), and Stangl, H., et al., (1998), iii) decreases in RCT, suggested by the generation of abnormally large, HDL-like particles and decreased biliary cholesterol levels due to absence of hepatic SR-BI activity, and iv) changes in other metabolic/organ systems which might influence the cardiovascular system. For example, there was significant accumulation of oil red O staining lipids in other tissues, including the myocardium, in the double, but not single, KO animals. In addition, at 5–6 weeks of age when the double KOs were studied, they were somewhat smaller (~20% lower weight) than single apoe KO controls.

While most did not exhibit overt signs of illness at that time, they all died suddenly around 8–9 weeks of age. Electrocardiographic studies indicated that premature death of the double KOs was due to progressive heart block (cardiac conduction defects) and histology revealed extensive cardiac fibrosis and narrowing or occlusion of the coronary arteries, suggesting myocardial infarction (MI) due to advanced atherosclerotic disease.

The anti-atherosclerotic effect of SR-BI expression in apoE KO mice is consistent with the recent reports that adenovirus- or transgene- Arai, T., et al., *J. Biol. Chem.* 274, 2366–2371 (1999), mediated hepatic overexpression of SR-BI in the cholesterol and fat-fed LDLR KO mouse reduces atherosclerosis. Thus, pharmacologic stimulation of endogenous SR-BI activity may be antiatherogenic, possibly because of its importance for RCT. The accelerated atherogenesis and loss of normal size HDL cholesterol in the double KOs resembles that reported for high-fat diet fed single apoE KO mice Zhang, S.H., et al., (1994), and Plump, A.S., et al., (1992); although those mice have far higher total plasma cholesterol levels (1800–4000 vs. ~600 mg/dl). Perhaps the similarities arise in part because the very high levels of large lipoproteins in the fat-fed single apoE KO might block the ability of SR-BI to interact with HDL and other ligands (functional SR-BI deficiency due to competition), or because of dietary suppression of hepatic SR-BI expression, Fluiter, K., et al., *J. Biol. Chem.* 273, 8434–8438 (1998).

Taken together with earlier work Krieger, M (1999), the current study provides compelling evidence for the proposal that, at least in rodents, SR-BI is an HDL receptor which mediates physiologically relevant selective cholesterol transport and plays a key role in controlling plasma lipoprotein and biliary cholesterol concentrations and RCT. It also influences HDL's structure, cholesterol's delivery to and utilization by cells (including those in steroidogenic tissues), reproductive and cardiovascular physiology and possibly other aspects of lipid metabolism, Hauser, H., et al., *Biochemistry* 37, 17843–17850 (1998). Because the in vitro activity, tissue distribution and regulation of human SR-BI, Murao, K., et al., (1997), Cao, G., et al., *J. Biol. Chem.* 272, 33068–33076 (1997), Calvo, D. et al., *J. Biol. Chem.* 268, 18929–18935 (1993), and Liu, J., et al., *J. Clin. Endocrinol. Metab.* 82, 2522–2527 (1997), resemble those of the mouse, SR-BI may become an attractive target for prevention of or therapeutic intervention in a variety of human diseases Acton, et al., (1996), Kozarsky, K.F., et al., (1997), Rigotti A., et al., (1997), Rigotti, A., et al., (1997), and Krieger, M., (1999).

TABLE II

Average lesion sizes in the aortic sinuses of mice deficient in SR-BI, apoE, or both.

Mean lesion size (mm$^2$)*

| Genotype | Aortic Root | Partial Valve Cusps | Valve Attachment Sites | Proximal Aorta | Overall Mean‡ |
|---|---|---|---|---|---|
| SR-BI$^{-/-}$ | 0.001 ± 0.002 (8) | 0.0003 ± 0.0008 (8) | 0 ± 0 (8) | 0 ± 0 (6) | 0.0004 ± 0.001 (6) |
| apoE$^{-/-}$ | 0.002 ± 0.002 (9) | 0.0006 ± 0.0009 (9) | 0.001 ± 0.002 (9) | 0.0002 ± 0.0003 (9) | 0.001 ± 0.002 (9) |
| SR-BI$^{-/-}$ apoE$^{-/-}$ | 0.10 ± 0.07 (7) | 0.07 ± 0.07 (7) | 0.02 ± 0.01 (6) | 0.02 ± 0.02 (6) | 0.04 ± 0.04 (6) |
| P value† | 0.0005 | 0.006 | 0.002 | 0.003 | 0.001 |

*Values are the means ± SD (number of animals indicated in parentheses).
‡Means of combined values from the regions of the aortic root partial valve cusps, valve attachment sites and proximal aorta.
†Lesion sizes in each region were compared using the Kruskall-Wallis test Modifications and variations of the methods and materials described herein will be obvious to those skilled in the art and are intended to be encompassed by the following claims. The teachings of the references cited herein are specifically incorporated herein.

We claim:

1. A transgenic mouse having homozygous disruptions in the SR-BI and ApoE genes that inhibit expression of active SR-BI and Apo-E, wherein the mouse is characterized by atherosclerotic plaque in the aortic sinuses and progressive heart block at between five and seven weeks of age.

2. A method for screening for compounds having an effect on disorders selected from the group consisting of cardiac fibrosis, myocardial infarction, defects in electrical conductance, atherosclerosis, unstable plaque, stroke and diseases associated with abnormal cardiac structure or function or elevated cholesterol or lipoprotein levels comprising administering the compound to a transgenic mouse having homozygous disruptions in the SR-BI and ApoE genes that inhibit expression of active SR-BI and Apo-E wherein the mouse develops atherosclerotic plaque in the aortic sinuses and progressive heart block at between five and seven weeks of age and determining the effect of the compound on cardiac fibrosis, myocardial infarction, defects in electrical conductance, atherosclerosis, unstable plaque, stroke, diseases associated with abnormal cardiac structure or function or elevated cholesterol or lipoprotein levels in the transgenic mouse relative to control mice not treated with compound.

3. The method of claim 2 wherein the mouse is an Apo E knockout mouse.

4. The method of claim 2 wherein the mouse does not express SR-BI.

5. The method of claim 2 wherein the mouse does not express active SR-BI.

6. The method of claim 3 wherein the mouse is an SR-BI and Apo E knockout.

7. The method of claim 2 wherein the transgenic mouse is treated with a compound which lowers the level of SR-BI.

8. The method of claim 2 wherein the transgenic mouse is treated with a compound which lowers the level of apolipoprotein E.

9. The method of claim 2 wherein the mouse is screened for alterations in levels of cholesterol or lipoproteins.

* * * * *

SEQUENCE LISTING

<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 1
tgaaggtggt cttcaagagc agtcct                                          26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 2
gattgggaag acaatagcag gcatgc                                          26

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 3
tatcctcggc agacctgagt cgtgt                                           25